United States Patent [19]

Armstrong et al.

[11] Patent Number: 5,629,424
[45] Date of Patent: May 13, 1997

[54] STEREOSELECTIVE ADSORPTIVE BUBBLE PROCESS

[75] Inventors: Daniel W. Armstrong, Rolla; Yubing Tang, Ballwin, both of Mo.

[73] Assignee: The Curators of the University of Missouri, Rolla, Mo.

[21] Appl. No.: 563,961

[22] Filed: Nov. 29, 1995

[51] Int. Cl.$^6$ .................... C07D 211/84; C07D 239/10
[52] U.S. Cl. .................... 544/316; 546/310; 548/491; 549/400; 560/39; 562/430; 562/433; 562/553
[58] Field of Search .................... 544/316; 546/310; 548/491; 549/400; 560/39; 562/430, 433, 553

[56] References Cited

U.S. PATENT DOCUMENTS 4,464,343  8/1984  Hitchcock et al. .................... 423/3

OTHER PUBLICATIONS

D. Armstrong et al. "Separation of Drug Stereoisomers by the Formation of β–Cyclodextrin Inclusion Complexes" Science, vol. 232 (1986) pp. 1132–1135.
D. Armstrong "Optical Isomer Separation by Liquid Chromatotography" Analytical Chemistry, vol. 59, No. 2, (1987) pp. 84A–91A.
D. Armstrong et al. "Foam Flotation Enrichment of Enantiomers" Analytical Chemistry, vol. 66, No. 23, (1994) pp. 4278–4282.
D. Armstrong et al. "Macrocyclic Antibiotics as a New Class of Chiral Selectors for Liquid Chromatography" Analytical Chemistry, vol. 66, No. 9 (1994) pp. 1473–1484.
"Cyclobond™ HPLC Columns—Cyclodextrin Stationary Phases For Chiral Separations and Highly Selective Achiral Separations" Commercail Literature, p. 7, 1995.
"Cyclobond I 2000™ HPLC Columns, The Second Generation Cyclolobond I Columns" Commercial Literature p. 8, 1995.
"Chirobiotic T™, Teicoplanin" Astec, Commercial Literature, 1995.
"For Superior Chiral Separation Chiral HPLC Column" Daicel Chemical Industries, Ltd., Commercial Literature (no date).
"Chirobiotic V™, Vanomycin" Astec, Commercial literature, 1995.
"The Pirkle–Concept" commercial literature (no date), p. 3.
Armstrong et al. "Foam Flotation Enrichment of Enantiomers" Advance ACS Abstracts, vol. 2, No. 20, (Oct. 15, 1994) pp. 4–5.

Primary Examiner—Joseph McKane
Attorney, Agent, or Firm—Senniger, Powers, Leavitt & Roedel

[57] ABSTRACT

Process for enriching the concentration of an enantiomer (or a diastereomer) in a mixture of optically active isomers. The process includes preparing a solution containing the mixture of the optically active isomers and a chiral collector in which the chiral collector and the enantiomer (or diastereomer) are associated with each other. A gas is bubbled through a pool of the solution to form a foam, the surfaces of the bubbles in the foam having the chiral collector and the enantiomer (or diastereomer) preferentially adsorbed thereto so that the concentration ratio of the optically active isomers at said bubble surfaces differs from that in the bulk of the pool. The foam is moved vertically through a column above the pool such that during said movement at least a portion of the bubbles comprising the foam break thereby allowing liquid to drain toward the pool to provide an internal reflux within the column.

17 Claims, 5 Drawing Sheets

STEREOSELECTIVE ADSORPTIVE BUBBLE PROCESS

BACKGROUND OF THE INVENTION

The present invention relates, in general, to a process for separating optical isomers, i.e., the enantiomers and diastereomers of a compound, and in particular, to a process and apparatus for separating the optical isomers by an adsorptive bubble technique.

Approximately 35% of all pharmaceutical products and agrochemicals (pesticides, herbicides, etc.) are racemic mixtures. In many instances, one of the isomers present in these mixtures have undesired effects and limit the overall effectiveness of the active species. For example, one of the isomers may present toxicity concerns, biodistribution problems, altered metabolism, and unwanted interactions.

Various techniques have been proposed to separate the enantiomers present in these racemic mixtures. According to one of these techniques, a diastereomeric derivative or complex of the racemate with a pure chiral molecule (selector) is prepared and this mixture is recrystallized several times. Although this technique works well for some mixtures, it tends to be tedious, time consuming and has narrow applicability. Also, it requires one additional separation step; the chiral selector (used to achieve the separation) must be removed from the final product.

Another technique which has been proposed to separate the enantiomers present in these racemic mixtures is biological or enzymatic resolution. In this technique, microorganisms or enzymes are used which preferentially degrade or react with one enantiomer of a racemate. Although selective, this approach is practical with only a limited number of compounds where the appropriate enzymes are available.

Differential complexation of a variety of isomers by an immobilized chiral stationary phase has also been proposed for separating enantiomers from a racemic mixture. See, for example, Armstrong, *Analytical Chemistry*, 59:84a–91a (Jan. 1987) and Armstrong et al., *Science*, 232:1132–1135 (1986). In these articles, the use of immobilized β-cyclodextrin and several other chiral stationary phases is reported for the enrichment of numerous compounds from such clinically useful classes as β-blockers, calcium-channel blockers, sedative hypnotics, antihistamines, anticonvulsants, diuretics, and synthetic opiates. Although this approach has applicability for a wide range of compounds, especially for analytical-scale separations, effective scale-up to relatively large amounts (i.e., industrial scale) is difficult, sensitive and expensive and requires trained personnel.

SUMMARY OF THE INVENTION

Among the objects of the invention, therefore, is the provision of a process which may be used to separate optical isomers, including, for example, optical isomers of commercial importance in the fields of pharmaceuticals, pesticides, herbicides, fragrance components and clinical analysis; the provision of such a process which may be used to enrich such isomers in relatively large-scale; the provision of such a process which is relatively cost-effective; the provision of such a process which has relatively wide-scale applicability; and the provision of an apparatus in which the enrichment or separation may be carried out.

Briefly, therefore, the present invention is directed to an adsorptive bubble separation process. The process comprises forming a solution containing a mixture of optically active isomers and a chiral collector, with the chiral collector being a compound having a chiral center and a structure capable of interacting with an enantiomer or diastereomer of the optical isomer mixture. A gas is bubbled through a pool of the solution to form bubbles with the surfaces of the bubbles having the chiral collector and the enantiomer or diastereomer preferentially adsorbed thereto so that the concentration ratio of the optically active isomers at said bubble surface differs from that in the bulk of the pool. The bubbles are allowed to move vertically through the gas-space above the upper surface of the pool and they are thereafter collapsed to form a liquid fraction which is separate from the pool.

DETAILED DESCRIPTION OF THE INVENTION

In accordance with the present invention, it has been discovered that effective and efficient separation of optical isomers can be carried out by adsorptive bubble separation techniques. Either foam fractionation, bubble fractionation, or tandem bubble and foam fractionation systems can be effectively utilized in the process of the present invention.

It will be understood by those skilled in the art that the method of invention is useful for enriching and concentrating optical isomers and that in many practical applications complete quantitative isolation of one optical isomer may not be a practical necessity. Thus, the terms "separation" and "separating" are used herein in their accepted sense of enrichment by modification of the optical isomer concentration ratio and do not necessarily imply quantitative isolation. Whatever the degree of separation desired, the process of the present invention provides an effective means to achieve it. Furthermore, although the optical isomers present in the mixture may be enantiomers or diastereomers, other facile techniques for separating diastereomers are known. Without limiting the scope of the present invention, therefore, the primary focus of the description set forth herein will be the separation or enrichment of an enantiomer present in a racemic mixture.

In the process of the present invention, a liquid feed mixture is prepared comprising an aqueous solvent, a mixture of at least two optical isomers, and a chiral collector. Typically, the aqueous solvent is water, but relatively small amounts of water-miscible components (e.g., alcohols, tetrahydrofuran, acetonitrile and salts) may be present, so long as they do not prevent or interfere with the adsorptive bubble fractionation process.

The chiral collector is a chiral compound which is at least partially water soluble and which selectively associates with an optical isomer present in the mixture. If the optical isomer is not, itself, a surfactant the chiral collector should be a surfactant capable of producing bubbles or a foam when associating with the optical isomer as a gas is bubbled through the solution. Enantioselectivity (or diastereomerselectivity) could result either from a difference in the association energy between the chiral collector and the two enantiomers (or diastereomers), from a difference in the surface adsorption of the two diastereomeric (chiral collector plus enantiomer or diastereomer) complexes, or from some combination of these two factors.

The chiral collectors interact with the optical isomer via a combination of ligand exchange interactions, charge-charge interactions, dipolar interactions, $\pi$ interactions, steric interactions, hydrophobic interactions, hydrogen-bonding interactions, or other types of interactions known to those of ordinary skill. As such, the chiral collectors have functional groups or a structure which provide at least three points of interaction with the optical isomer of interest. The points of interaction may be provided, for example, by (i) hydrogen-bonding groups such as carbonyl, hydroxyl, amine, sulfoxide and amide groups, with hydroxyl and amine groups being the presently preferred hydrogen-bonding groups, (ii) acidic groups such as carboxylates, sulfonates, sulfates, phosphates, phosphonates, phosphenates, and phenolates with carboxylic acids being the presently preferred acidic groups, (iii) basic groups such as protonated amines which include, for example, ammonium and alkyl and aryl ammonium groups, (iv) dipolar interactive groups such as carbonyl, amide, and sulfonamide groups, (v) aromatic rings (carbo- or heterocyclic, substituted or unsubstituted) which provide $\pi$ interaction with the optical isomer of interest, and (vi) a hydrophobic region consisting of one or more non-polar moieties located in close proximity to one another such as a hydrophobic cavity, i.e., a region of the chiral collector which is generally concave in shape (when viewed in three dimensions), is more hydrophobic than the solution in which the chiral collector is dissolved, and is capable of forming a complex with the isomer of interest.

In a preferred embodiment of the present invention, the chiral collector has a sufficient number of the requisite groups or moieties and in the proper orientation such that simultaneous interactions can occur with chiral molecules. Also, the chiral collector should be surface-active for most separations. Chiral collectors falling within this class include many derivatized cyclodextrins, amino acids (native or derivatized), antibiotics (native or derivatized), proteins (native or derivatized), peptides (native or derivatized), carbohydrates (native or derivatized), crown ethers, specially designed synthetic compounds and combinations thereof. In this context, derivatization means attachment of a functional group or moiety which (i) provides one or more points of interaction as described in detail in the paragraph immediately preceding this paragraph, or (ii) modifies or introduces surface-activity.

In general, the amount of chiral collector in the liquid feed mixture should be sufficient to create a continuous foam. In addition, the chiral collector is preferably present in a molar excess relative to the optical isomer with the molar ratio of the two being in the range, for example, of about 1:1 to about 5:1 (collector:isomer). Large molar excesses of the collector (e.g., >10:1) can result in a diminishing enrichment or yield and are presently not preferred.

Adsorptive bubble separation is effected by passing a gas through a pool of the liquid mixture. The gas should be essentially inert with respect to the components of the feed mixture. Typically, air or nitrogen may be used.

On passing of the gas through the feed mixture, bubbles are formed and a layer of surfactant collects at the gas liquid interface on the bubble surfaces. As previously noted, the surfactant may be the chiral collector or the optical isomer. In either event, the chiral collector interacts with at least one of the optical isomers in the mixture and the interacting pair become adsorbed on the bubble surfaces. As a result of the selectivity of the chiral collector for one of the optical isomers or as a result of different surface adsorption characteristics, one optical isomer is preferentially adsorbed on the bubble surfaces. This has the effect of concentrating at least one of the optical isomers in the foam and at least one of the optical isomers in the liquid feed mixture, either of which may be the isomer of interest.

Where optical isomer separation is effected by bubble fractionation, passage of bubbles up through the liquid mixture results in concentration of one of the optical isomers of the mixture in a layer at the upper surface of the liquid, while in foam fractionation, that isomer is transported from the liquid by foam rising from the upper liquid surface. Preferably, foam fractionation is employed and the foam which rises from the upper liquid surface is separated from the liquid mixture. If the optical isomer of interest is concentrated in the foam, it is then collected by collapsing the separated foam at a location other than the liquid surface and separating the chiral collector from the isotope of interest by liquid-liquid extraction, precipitation by evaporation, or other standard techniques known to those of ordinary skill. It is preferred that the chiral collector have a different solubility than the optical isomer (in water or organic solvent), different partitioning characteristics or a different volatility to readily enable separation of the chiral collector from the isomer. Also, it is preferred that the chiral collector be stable through the fractionation and separation steps of the present invention to enable recycle and reuse of the chiral collector.

Although temperature of operation is not narrowly critical, lower operating temperatures generally provide greater selectivity. Depending upon the selectivity, therefore, the process may be carried out at room temperature. For some systems, however, selectivity at room temperature will be insufficient and temperatures of about 10° C. or less are preferred.

Figure 1:
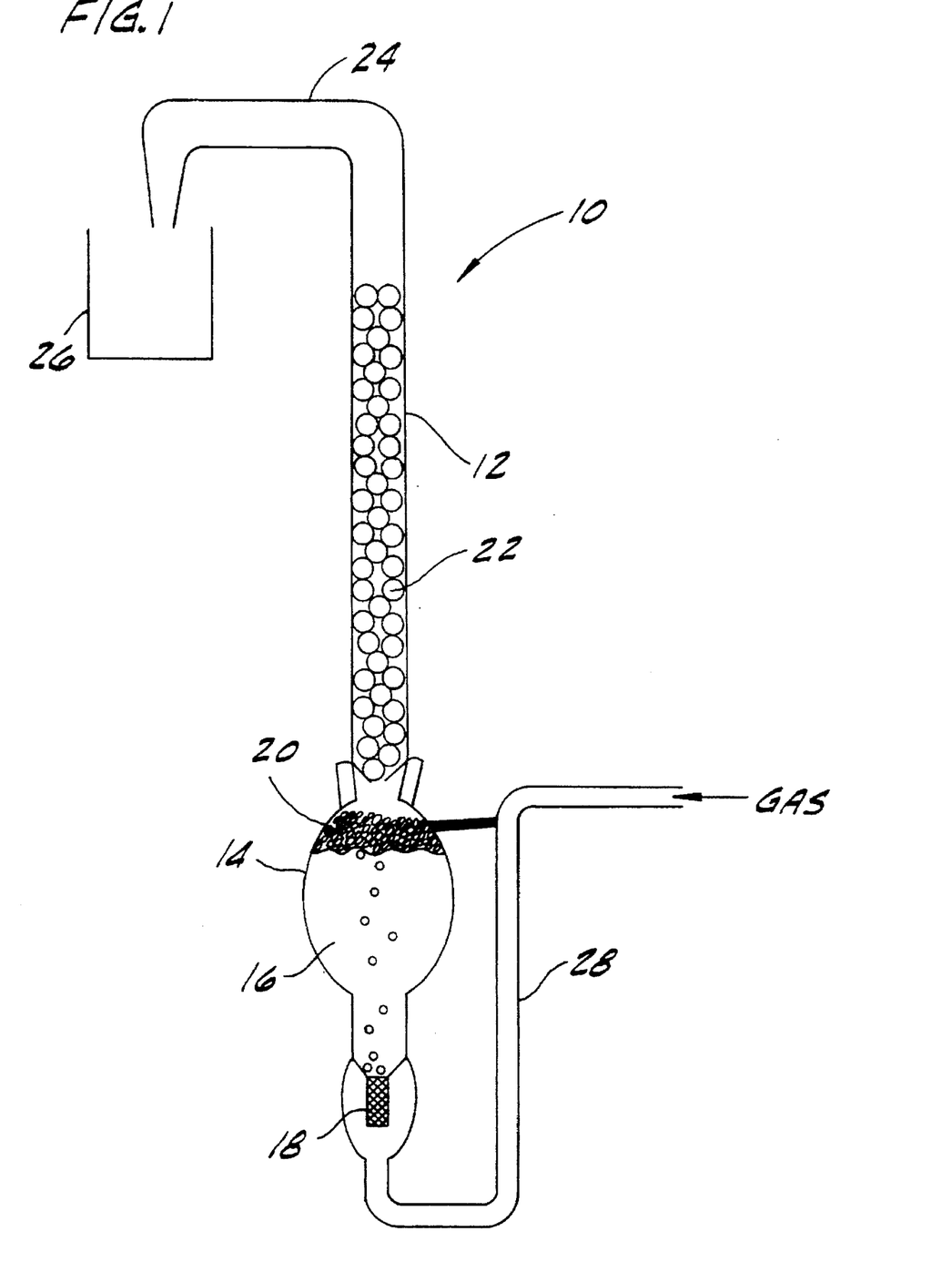
FIG. 1 is a schematic view of a laboratory-scale apparatus for adsorptive bubble separation of optical isomers in accordance with the present invention.

Illustrated schematically in FIG. 1 is an apparatus for separation of optical isomers by foam fractionation. The apparatus, generally designated by reference numeral 10 comprises a column 12 disposed over a vessel 14. Within vessel 14 is a pool 16 of the liquid mixture which comprises a chiral collector and two or more optical isomers to be separated. Gas is introduced into pool 16 through a sparger 18 (such as a fine, porous glass frit) creating bubbles which pass through the pool and form a foam phase 20 above the upper surface of pool 16. The foam preferably consists of bubbles having an average diameter of less than about 5 millimeters, more preferably less than about 3 millimeters, and even more preferably less than about 1 millimeter. Foam 20 moves upward into column 12, contacts packing material 22 and then through a U-bend 24 into foam beaker 26 where the foam is collapsed by allowing it to rest, adding a miscible or immiscible solvent, heating or other conventional techniques. The packing material may be any conventional, inert packing material such as glass metal or plastic beads, helices or coils which increase the surface area of the column and assist in controlling the flow rate of the foam, thereby reducing the size of the foam bubbles and the water content of the foam. Gas is fed to sparger 18 through tube 28.

Preferably, the gas flow rate is initially adjusted so that the foam remains equilibrating in the column under reflux conditions for several minutes, e.g., about 5 to about 30 minutes. During this period, foam is rising from the liquid surface and passing through the packing material. Simultaneously, bubbles in the rising foam break thereby releasing liquid which flows back down through the packing material and into the pool 16. This countercurrent process is analogous to total reflux conditions in a fractional distillation column. After this initial period, the gas flow rate is increased and foamed solution is collected in foam beaker 26. During the period in which foam is being collected, however, partial reflux of the mixture continues with the volume ratio of liquid moving up the column as a foam to liquid draining toward the pool preferably being at least about more preferably at least about 1:1, and still more preferably at least about 5:1, 10:1, 50:1 or even 100:1.

The optical isomer of interest may be found in the overhead product or in pool upon cessation of the bubbling as a bottoms product. If desired, the process may be repeated using the overhead or the bottoms product as the starting solution.

The following example will illustrate the invention.

EXAMPLE

In this example, enantiomeric enrichments were obtained for each of two different compounds using the foaming device used shown in FIG. 1 in which the foam column was 32 cm long, the glass beads were 0.7 cm diameter, the sample chamber could hold up to 200 ml of aqueous sample solution, and the gas flow rate (i.e., $N_2$ or air) was controlled via a flow control valve. The structures of the racemic compounds resolved are as follows:

(SQ 30,840)

(SQ 31,236)

Stock solutions of the compounds were made into stock solutions in ethanol (or in acetonitrile for those analytes analyzed using vancomycin) at a concentration of 12 mg/mL). Solutions of the chiral collector were made in distilled water or buffer at concentrations ranging from 0.01% to 1%. One milliliter of the racemic mixture solution and 19 mL of chiral collector solution were placed into the foaming chamber, and the foaming column was attached to the sample chamber via a ground-glass joint. Air was used to generate bubbles from the bottom of the chamber. The height of the foam in the column was controlled by adjusting the air flow rate with a fine control valve. In general, dry foam formed after a period of controlled reflux gives the best results. The glass beads also seem to help produce a finer, slower rising foam. The foam bubbles tend to break on the way up the column thereby producing a thin film of liquid that flows down the column (i.e., opposite to the foam migration). The airflow rate was adjusted so that a steady countercurrent condition was produced (somewhat analogous to that of a fractional distillation column). At this point no foam passes to the receiver. A foam fraction was collected either by slightly increasing the flow rate to force some foam into one receiver or by using a syringe connected to a long thin Teflon tube on the needle to reach the top layer of the foam in the column. In some experiments, 3 mL of a foam fraction and 12 mL of fresh chiral collector solution were used for a series of consecutive runs. Most enantiomeric ratios in the foam fractions were determined by HPLC. A Shimadzu LC 6A liquid chromatography with a variable-wavelength detector and a C-R3A Chromatopac data system were used for all data analysis. The chromatographic conditions for the separation of all compounds studied are listed in Table 1. The UV detection wavelength was 254 nm for all analytes except for the N-t-BOC amino acids, which was 225 nm. The warfarin peaks overlapped with the chiral collector, thus solid phase extraction on a silica cartridge was employed to remove the chiral collector before HPCL injection. The silica cartridge was washed with 3–5 mL of diethyl ether before the warfarin fraction was loaded, and then warfarin was eluted from the cartridge with diethyl ether and collected for analysis. Foam fractions of other compounds were injected directly on the chiral stationary phase containing LC column. The enantiomeric purity of dansyl-tryptophan and dansyl-phenylalanine were determined directly on a Waters Quanta 4000 CE apparatus equipped with a 254 nm lamp and a 50 μm (i.d.)×32 cm (24 cm to detector) fused silica capillary. The run buffer contained 0.1M, pH 6 phosphate buffer plus 2 mM vancomycin as the chiral selector.

TABLE 1

Analytical Separation Conditions for Enantiomeric Excess Determinations

| Racemate | Structure | Column | Mobile Phase[f] or Run Buffer |
|---|---|---|---|
| warfarin | | Cyclobond I[b] | acetonitrile/methanol/acetic acid/triethylamine (90/10/0.004/0.004) |
| SQ 30,840 | | Cyclobond I RSP[c] | aqueous buffer[g]/acetonitrile (80/20) |
| SQ 31,236 | | Cyclobond I SP[d] | aqueous buffer[g]/acetonitrile (85/15) |
| N-t-Boc-chlorophenylalanine | | Cyclobond I RSP[c] | aqueous buffer[h]/acetonitrile (95/5) |
| N-t-Boc-phenylalanine | | Cyclobond I RSP[c] | aqueous buffer[h]/acetonitrile (93/7) |
| leucine[a] | | Cyclobond I[b] | acetonitrile/methanol/acetic acid/triethylamine (90/10/0.4/2) |
| methionine[a] | | Cyclobond I[b] | acetonitrile/methanol/acetic acid/triethylamine (96/4/0.6/1) |
| phenylalanine[a] | | Cyclobond I[b] | acetonitrile/methanol/acetic acid/triethylamine (90/10/0.4/1.2) |

TABLE 1-continued

Analytical Separation Conditions for Enantiomeric Excess Determinations

| Racemate | Structure | Column | Mobile Phase[f] or Run Buffer |
|---|---|---|---|
| tryptophan[a] | (structure: tryptophan) | Cyclobond I[b] | acetonitrile/methanol/acetic acid/ triethylamine (96/4/0.6/1.2) |
| dansyl-tryptophan | (structure: dansyl-tryptophan) | fused silica[e] | 0.1M phosphate buffer (pH 6) containing 3 mM vancomycin[24] |
| dansyl-phenylalanine | (structure: dansyl-phenylalanine) | fused silica[e] | 0.1M phosphate buffer (pH 6) containing 3 mM vancomycin[24] |

[a]Before analysis these amino acids were derivatized with AQC; fluorescent tagging agent. See S. Armstrong et al., Journal of Analytical Chem., Vol. 62, 914 (1990) for the complete procedure.
[b]Cyclobond I refers to a 25 cm (4.6 cm i.d.) native β-cyclodextrin HPLC column.
[c]Cyclobond I RSP refers to a 25 cm (4.6 cm i.d.) rac-hydroxypropyl-β-cyclodextrin HPLC column.
[d]Cyclobond I SP refers to a 25 cm (4.6 cm i.d.) (S)-hydroxypropyl-β-cyclodextrin HPLC column.
[e]This column is a 50 μm (i.d.) × 32 cm (24 cm to detector) fused silica capillary used in capillary electrophoresis.
[f]Mobile phase compositions are given as volume ratios.
[g]The buffer consisted of 1% triethylammonium acetate (aq), pH 4.1.
[h]The buffer consisted of 1% triethylammonium acetate (aq), pH 7.1.

General conditions for the alkylhydroxyproline and digitonin chiral collector experiments were as follows: 5mL of 0.02% (unless indicated otherwise) surfactant solution (n-heptyl-L-hydroxyproline, for example) in water was mixed with 0.25 mL of stock solutions of leucine (2 mg/mL), methionine (2.32 mg/mL), phenylalanine (2.6 mg/mL), and tryptophan (2.8 mg/mL). Approximately 4.4 mg of cupric acetate was added to the solution. When foaming was completed, the residual solution was analyzed as outlined below. All amino acids were derivatized with (6-aminoquinolyl)-N-hydroxysuccinimidyl carbamate (AQC) and separated via HPLC as indicated in Table I. This achiral derivatization procedure for amino acids and the enantioselective separation method has been described previously.

A small aliquot of this sample was analyzed (by chiral HPLC and/or circular dichroism) to determine the enantiomeric ration of the test solute. Nine additional milliliters of foam solution was then taken. The total solution (12 ml) was transferred to an identical foaming device for the next cycle. Using this procedure we were able to start with racemic SQ 30840 and achieve a solution containing 81% of one enantiomer vs 19% of the other. In the case of SQ 31236 a 2:1 enantiomeric enhancement was found.

Enantiomeric enrichment conditions and results using various derivatized cyclodextrins, alkylated amino acids, digitonin, and some antibiotics are set forth in Tables 2 and 3. Table 2 summarizes the data for different derivatized cyclodextrin chiral collectors while Table 3 does the same for other chiral collectors. Note that the alkylproline chiral collectors (Table 3) were used in a "ligand exchange" format. Hence, copper (II) salts were dissolved in solution before foaming.

TABLE 2

Foam Flotation Conditions and Enantiomeric Enrichments Using Derivatized Cyclodextrin Collectors

| Racemates | Collectors[a] | Collector Concentration (G/100 mL) | temp (°C.) | foaming column ht (cm) | No. Passes through column | enantiomeric ratio[b] | ee[c] (%) |
|---|---|---|---|---|---|---|---|
| warfarin | PM-β-CD | 1 | 23 | 25 | 1 | 60/40 | 20 |
|  | DM-β-CD | 1 | 23 | 25 | 1 | 44/56 | 12 |
| SQ 30,840 | Oct-β-CD | 1 | 23 | 25 | 1 | 56/44 | 12 |

TABLE 2-continued

Foam Flotation Conditions and Enantiomeric Enrichments Using Derivatized Cyclodextrin Collectors

| Racemates | Collectors[a] | Collector Concentration (G/100 mL) | temp (°C.) | foaming column ht (cm) | No. Passes through column | enantiomeric ratio[b] | ee[c] (%) |
|---|---|---|---|---|---|---|---|
| | HP-β-CD | 1 | 23 | 25 | 1 | 66/34 | 32 |
| SQ 31,236 | HP-β-CD | 1 | 23 | 25 | 1 | 46/54 | 8 |
| N-t-BOC-chlorophenylalanine | PM-β-CD | 0.05 | 23 | 25 | 1 | 47/53 | 6 |
| | PM-β-CD | 0.05 | 4 | 25 | 1 | 37/63 | 26 |
| N-t-BOC-phenylalanine | PM-β-CD | 0.05 | 23 | 25 | 1 | 41/59 | 18 |
| | PM-β-CD | 0.05 | 4 | 25 | 1 | 18/82 | 64 |
| | PM-β-CD | 0.05 | 4 | 40 | 1 | 12/88 | 76 |
| | DM-β-CD | 0.05 | 4 | 25 | 1 | 48/52 | 4 |

[a]Abbreviations: PM-β-CD = heptakis-2,3,6-tri-O-methyl-β-cyclodextrin; DM-β-CD = heptakis-2,6-di-O-methyl-β-cyclodextrin; Oct-β-CD = a mixture of β-cyclodextrin monooctyl and dioctyl esters; HP-β-CD = hydroxypropyl-β-cyclodextrin.
[b]This is the peak area ratio of first peak/second peak.
[c]Enantiomeric excess (ee) is defined as follows: ee = $[(E_1 - E_2)/(E_1 + E_2)] \times 100\%$, where $E_1$ is the amount of the enantiomer present in higher concentrations and $E_2$ is the amount of the enantiomer present in lower concentration.

TABLE 3

Foam Flotation Conditions and Enantiomeric Enrichments Using Chiral Collectors Not Related to Cyclodextrin

| Racemates | Collectors[a] | Collector Concentration (G/100 mL) | temp (°C.) | foaming column ht (cm) | No. Passes through column | enantiomeric ratio[b] | ee[c] (%) |
|---|---|---|---|---|---|---|---|
| leucine | Hep-HProl | 0.4 | 23 | 25 | 1 | 35/65 | 30 |
| | Dodec-HProl | std soln | 23 | 25 | 1 | 46/54 | 8 |
| methionine | Hep-Hprol | 0.2 | 23 | 25 | 1 | 42/58 | 16 |
| phenylalanine | Hep-HProl | 0.2 | 23 | 25 | 1 | 41/59 | 18 |
| tryptophan | digitonin | atd soln | 23 | 25 | 1 | 47/53 | 6 |
| dansyl-tryptophan | vancomycin | 0.06 | 4 | 25 | 1 | 41/59 | 18 |
| dansyl-phenylalanine | vancomycin | 0.06 | 4 | 25 | 1 | 47/53 | 6 |

[a]Abbreviations: Hep-HProl = n-heptyl-L-hydroxyproline; Dodec-HProl = n-dodecyl-L-hydroxyproline.
[b]This is the peak area ratio of first peak/second peak.
[c]Enantiomeric excess (ee) is defined as follows: ee = $[(E_1 - E_2)/(E_1 + E_2)] \times 100\%$, where $E_1$ is the amount of the enantiomer present in higher concentration and $E_2$ is the amount of the enantiomer present in lower concentration.

Figure 2:
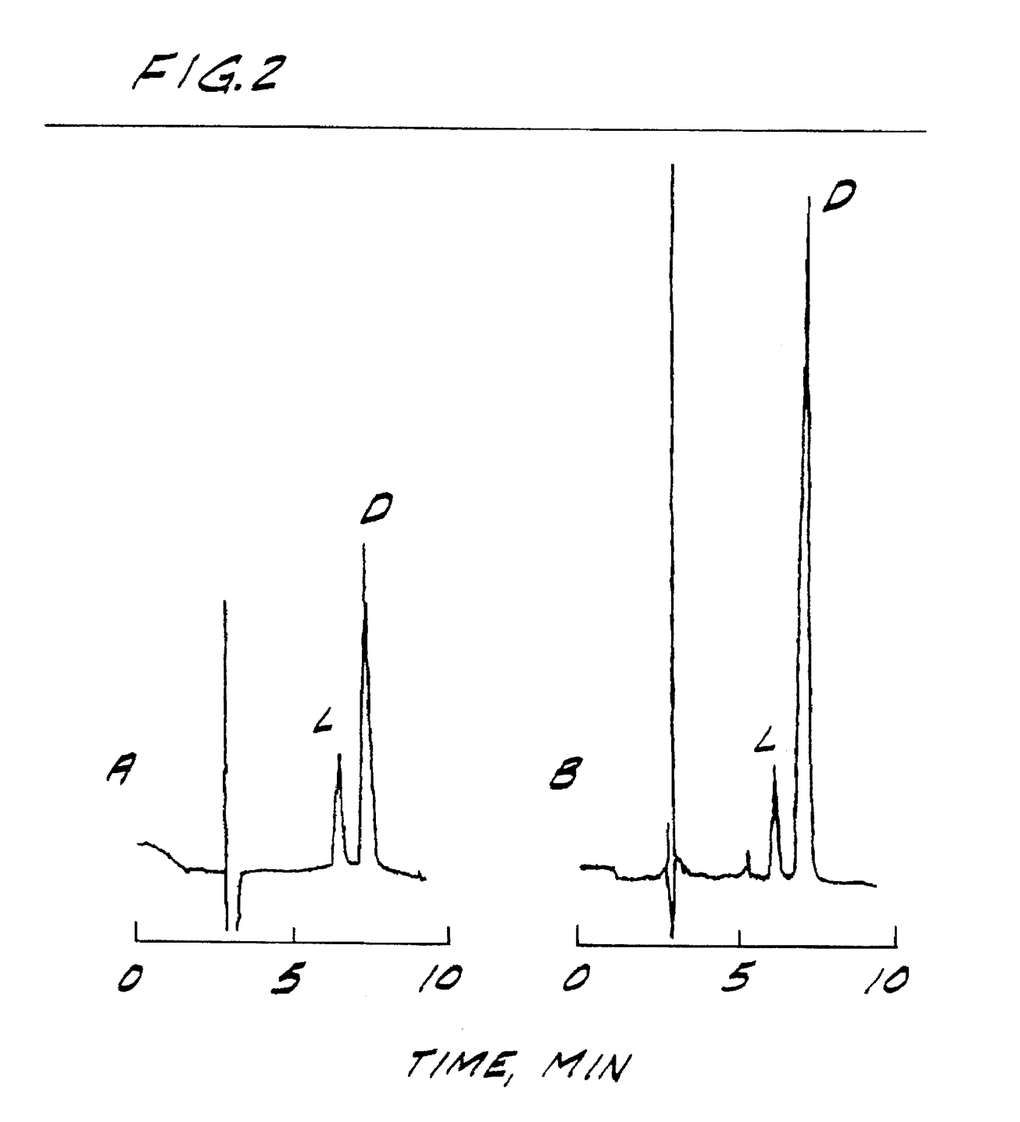
FIG. 2 is a LC chromatogram showing the enantiomeric enrichment of D-N-t-BOC-phenylalanine (i.e., the second peak in both chromatograms) using (a) a 25 or (b) a 40 cm long foam column as described in the Example. The experiment was carried out at 4° C. using permethyl-β-cyclodextrin as the chiral collector, under total reflux conditions. The analytical LC chiral separations were done on a Cyclobond I-RSP column (see Table 1 for conditions).
Figure 3:
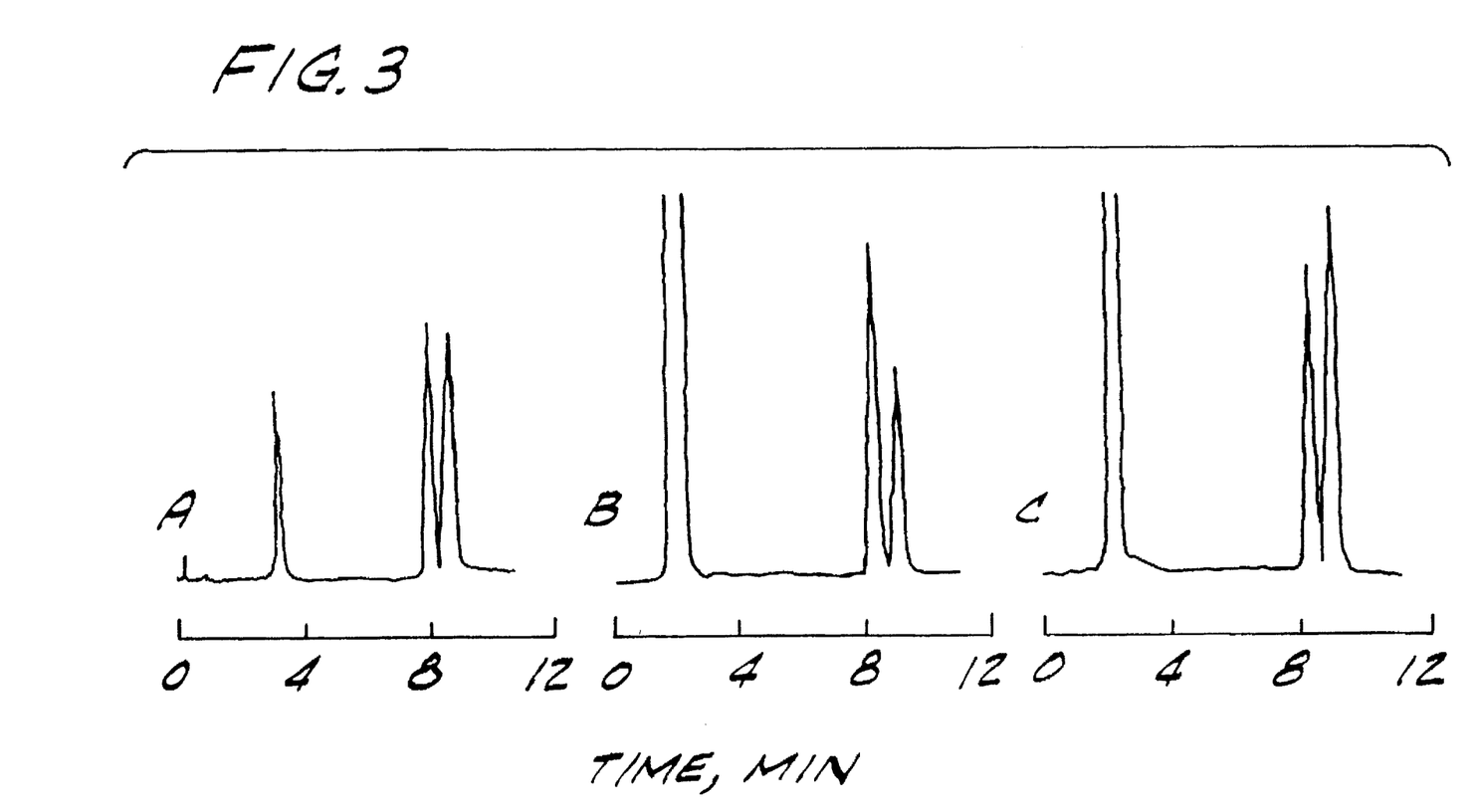
FIG. 3 is a series of LC chromatograms: (A) separation of racemic warfarin starting material, (B) foam enriched product using permethyl-β-cyclodextrin as a chiral collector, and (C) foam-enriched product using heptakis(2,6-di-O-methyl)-β-cyclodextrin as a chiral collector as described in the Example. Experiments B and C were done at room temperature using a 25 cm long packed foam column. The analytical separations were done on a Cyclobond I HPLC column (see Table 1 for conditions).

A number of things are evident from the data presented in Tables 2 and 3. First and foremost, it is clearly demonstrated that enantiomeric enrichments are possible using adsorptive bubble processes. While enantiomeric enrichments after a single pass through the column at room temperature (ee's= 4–30) are not extraordinary, they are easily enhanced by modifying certain experimental conditions. As can be seen in Table 2 for N-t-BOX-chlorophenylalanine and N-t-BOC-phenylalanine, lowering the temperature of the foam flotation column and sample reservoir to 4° C. results in a significant increase in the enantiomeric excess. Increasing the length of the foam column from 25 to 40 cm also appeared to enhance the effectiveness of the separation (Table 2 and FIG. 2). The results for warfarin were particularly interesting. This was because enrichments were produced with two different cyclodextrin derivatives but they gave opposite enantiomeric selectivity (FIG. 3 and Table 2). This was the only case where an enantioselective reversal was observed. Enantiomeric enrichments also can be enhanced by repeating the foam fractionation process with a series of identical devices.

Figure 4:
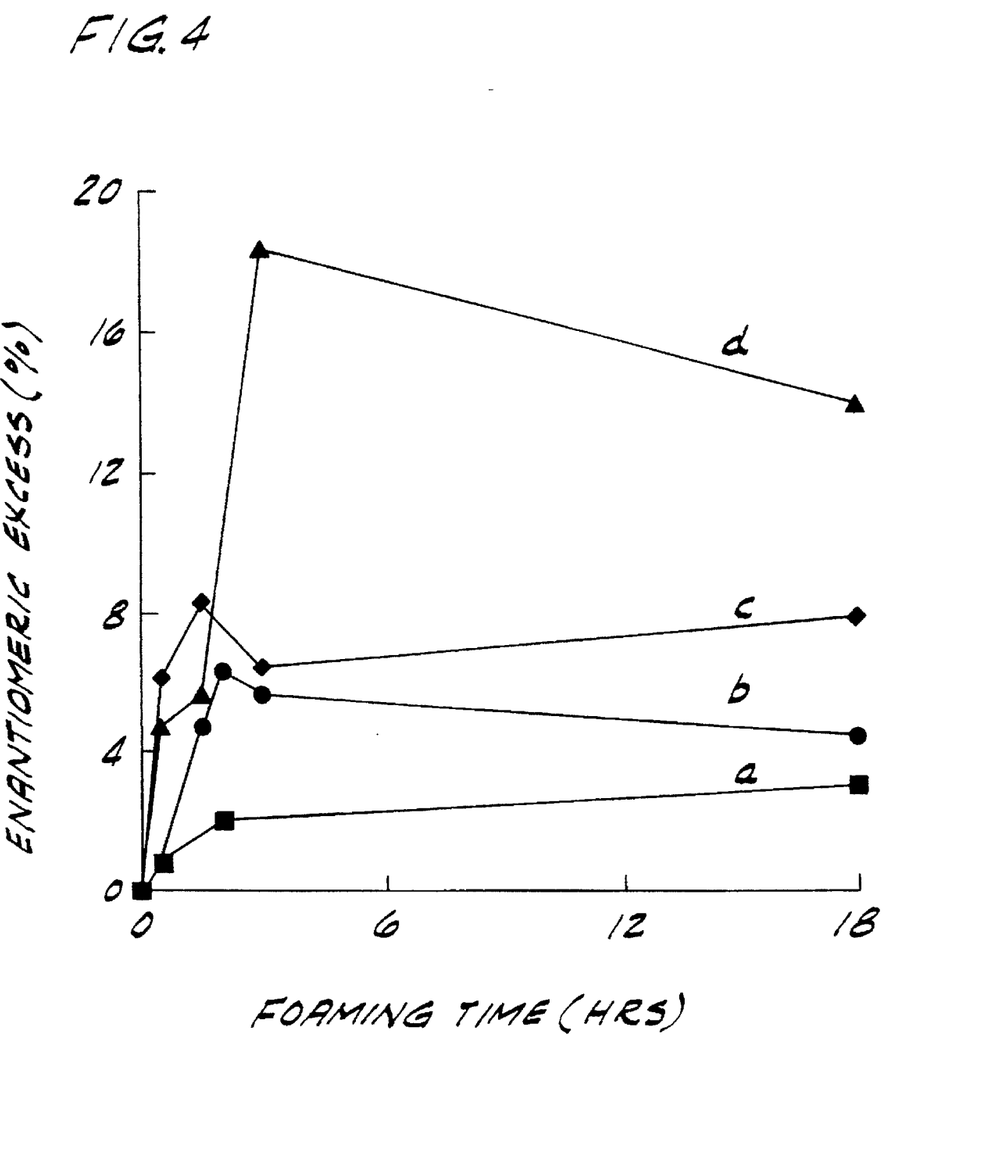
FIG. 4 shows the effect of reflux equilibration time and concentration of the chiral collector on the enantiomeric enrichment of D-N-t-BOC-phenylalanine as described in the Example. Each curve represents a different concentration of the permethyl-β-cyclodextrin chiral collector: (a) 1%, (b) 0.1%, (c) 0.01%, and (d) 0.05%. Experiments were done at room temperature using a 25 cm long packed foam column. The chiral collector was permethyl-β-cyclodextrin.

It appears that there are some similarities between the operation of a foam fractionation column and a fractional distillation column. For example, longer columns (Table 2) and additional fractionation cycles (Tables 4 and 5) give a more highly enriched product. The best results are obtained in both systems when the columns are operated under "reflux" conditions (where there is a countercurrent flow in the column). As shown in FIG. 4, allowing the foam system to equilibrate or reflux for a period of time (before sample removal) enhances the enrichment process. However, after this particular system has equilibrated for a period of time (~25–90 min), there is no benefit (i.e., no further enrichments) in extending the process.

TABLE 4

Effect of Repeated Passes Through a Foam Flotation Column on the Enantiomeric Enrichment of SQ 30 840[a]

| Peak Area | Cycle Number | | | | | | | |
|---|---|---|---|---|---|---|---|---|
| | 1 | 2 | 3 | 4 | 5 | 6 | 7 | 8 |
| First Peak | 2.31 | 2.44 | 1.39 | 1.22 | 1.18 | 1.23 | 0.82 | 0.68 |
| Second Peak | 2.08 | 1.55 | 0.76 | 0.56 | 0.55 | 0.44 | 0.24 | 0.16 |
| Peak Ratio | 1.11 | 1.61 | 1.83 | 2.18 | 2.15 | 2.80 | 3.42 | 4.25 |

[a]Hydroxypropyl-β-cyclodextrin was used as the chiral collector (See Experimental Section and Table II for further experimental details.

TABLE 5

Effect of Repeated Passes Through a Foam Flotation Column on the Enantiomeric Enrichment of SQ 31,236[a]

| Peak Area | Cycle Number | | | | | |
|---|---|---|---|---|---|---|
| | 1 | 2 | 3 | 4 | 5 | 6 |
| First Peak | 3.61 | 2.66 | 1.97 | 1.48 | 1.22 | 0.64 |
| Second Peak | 4.26 | 3.42 | 2.66 | 2.16 | 2.55 | 1.43 |
| Peak Ratio | 1.18 | 1.28 | 1.35 | 1.46 | 2.09 | 2.23 |

[a]Hydroxypropyl-β-cyclodextrin was used as the chiral collector (See Experimental Section and Table II for further experimental details.

Figure 5:
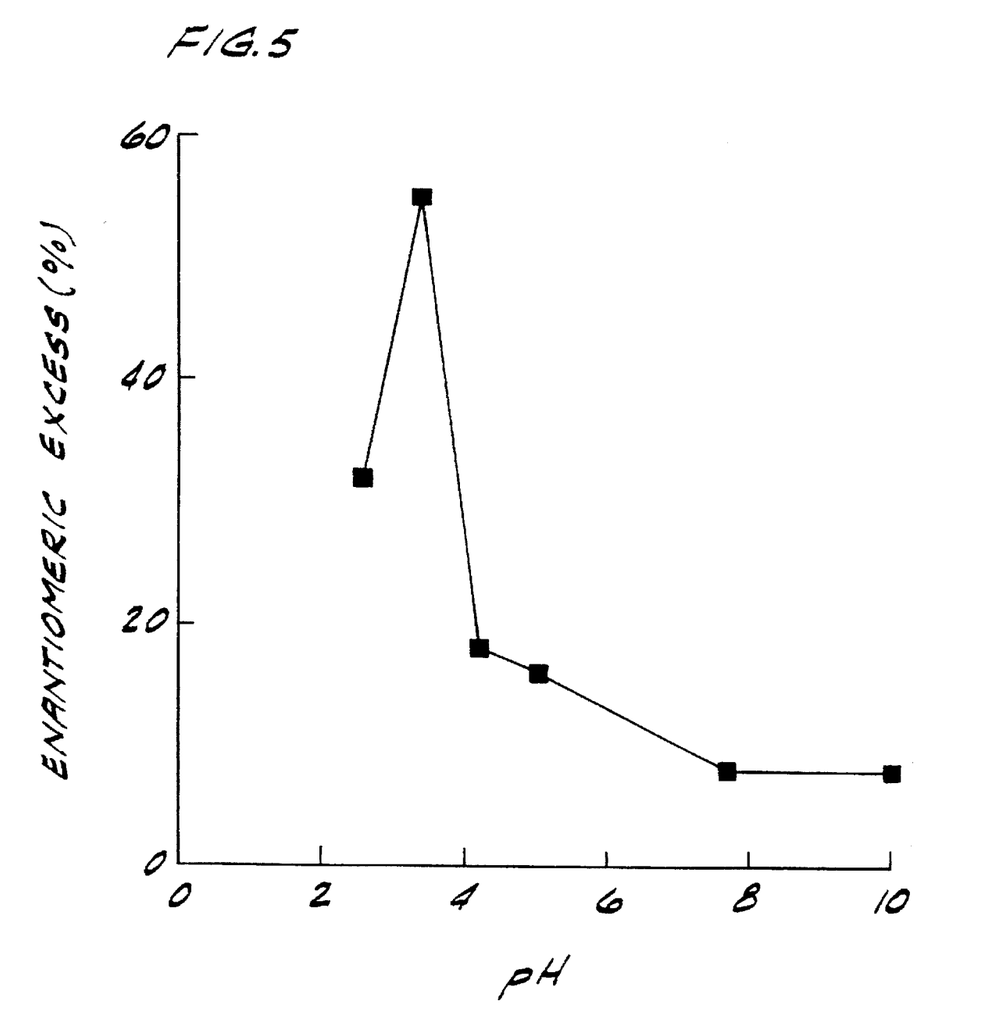
FIG. 5 shows pH dependance for the enantiomeric enrichment of N-t-BOC-phenylalanine as described in the Example. The buffer was 0.01% triethylammonium acetate.

FIG. 4 also shows that the concentration of the chiral collector affects the enantiomeric enrichment. There appears to be an optimum concentration of chiral collector and racemate for every system. The enantiomeric excess decreases if the system is operated with too much or too little chiral collector. The optimum concentrations of chiral collector and racemate must be determined empirically. As yet we have found no recognizable trend or theory that allows a prediction of the best absolute and/or relative concentrations. Another factor that affects the enantiomeric excess is the pH of the sample solution. FIG. 5 indicates that L-N-t-BOC-phenylalanine is more highly enriched at pH's near 3 than at more basic pH's. This is not surprising in view of past enantioseparation results in reversed phase HPLC. The pH controls the ionization state of the analyte and in some cases of the chiral selector. Consequently, enantioselective interactions are strongly pH dependent. It is not unusual in HPLC and capillary electrophoresis for an enantiomeric separation to occur at one pH and not at another. Clearly, optimization of the pH can be as important in foam flotation as in most other water-based enantioseparation techniques.

In general, factors that appeared to affect this water-based separation include the following: (a) column length, (b) column geometry and packing, (c) gas flow rate, (d) column geometry and packing, (c) gas flow rate, (d) concentration of the chiral collector and the racemate, (e) nature of the chiral collector, (f) temperature, (g) pH, (h) reflux time, (i) foam dryness, and (j) the presence of other materials in the sample (e.g., miscible organic solvents, salts, etc.).

Materials. Heptakis(2,6-di-O-methyl)-β-cyclodextrin was purchased from Sigma (St. Louis, Mo.), permethyl-β-cyclodextrin was obtained from Cyclolab R&D Laboratory (Budapest, Hungary), and hydroxypropyl-β-cyclodextrin was obtained from Consortium Fur Elektrochemische Industrie GMBH. Significantly, no commercial derivatized cyclodextrins are pure; they are composed of mixtures of homologues and isomers. Warfarin, D- and L-N-t-BOC-phenylalanine, D- and L-N-t-BOC-chlorophenylalanine, dansyl-D,L-tryptophan, dansyl-D,L-phenylalanine, N-heptyl-L-hydroxyproline, vancomycin, and digitonin were purchased from Sigma. SQ 30,840 and SQ 31,236 were obtained from Squibb (New Brunswick, N.J.). All solvents were obtained from Fisher Scientific (Fair Lawn, N.J.). The silica cartridges for solid phase extraction were purchased from Alltech (Deerfield, Ill.). All HPLC columns were obtained from Advanced Separation Technology Inc. (Whippany, N.J.). Pyrex gas dispersion tubes and other glassware were obtained from Fisher Scientific.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What is claimed is:

1. A process for enriching the concentration of an enantiomer or a diastereomer in a mixture of optically active isomers, the process comprising:

preparing a solution containing the mixture of the optically active isomers and a chiral collector in which the chiral collector and the enantiomer or diastereomer are associated with each other, bubbling a gas through a pool of the solution to form a foam, the surfaces of the bubbles in the foam having the chiral collector and the enantiomer or diastereomer preferentially adsorbed thereto so that the concentration ratio of the optically active isomers at said bubble surfaces differs from that in the bulk of the pool, moving said foam vertically through a column above the pool such that during said movement at least a portion of the bubbles comprising the foam break thereby allowing liquid to drain toward the pool to provide an internal reflux within the column.

2. The process of claim 1 wherein the column is packed with a packing material.

3. The process of claim 1 wherein the column is packed with glass, plastic or metal spheres, helices or coils.

4. The process of claim 1 wherein the foam exits the column and is collected as an overhead product and, as the foam exits the column, the volume ratio of liquid moving up the column as a foam to liquid draining toward the pool is at least about 1:5.

5. The process of claim 1 wherein the foam exits the column and is collected as an overhead product and, as the foam exits the column, the volume ratio of liquid moving up the column as a foam to liquid draining toward the pool is at least about 1:1.

6. The process of claim 1 wherein the foam exits the column and is collected as an overhead product and, as the foam exits the column, the volume ratio of liquid moving up the column as a foam to liquid draining toward the pool is at least about 5:1.

7. The process of claim 1 wherein the foam exits the column and is collected as an overhead product and, as the foam exits the column, the volume ratio of liquid moving up the column as a foam to liquid draining toward the pool is at least about 10:1.

8. The process of claim 1 wherein the foam exits the column and is collected as an overhead product and, as the foam exits the column, the volume ratio of liquid moving up the column as a foam to liquid draining toward the pool is at least about 50:1.

9. The process of claim 1 wherein the foam exits the column and is collected as an overhead product and, as the foam exits the column, the volume ratio of liquid moving up the column as a foam to liquid draining toward the pool is at least about 100:1.

10. A process for enriching the concentration of an enantiomer in a mixture of optical isomers, the process comprising:

preparing a solution containing the mixture of the optically active isomers and a chiral collector in which the chiral collector and the enantiomer are associated with each other and in which there are simultaneously at least 3 points of interaction between the chiral collector and the enantiomer, bubbling a gas through a pool of the solution to form bubbles, the surfaces of the bubbles having the chiral collector and the enantiomer preferentially adsorbed thereto so that the concentration ratio of the optical isomers at said bubble surface differs from that in the bulk of the pool, and moving said bubbles vertically through the area above the upper surface of the pool.

11. The process of claim 10 wherein the chiral collector has surface-active properties.

12. The process of claim 10 wherein after said moving step, the bubbles are recovered as an overhead product containing a mixture of optical isomers which is enriched in one of the enantiomers as compared to the starting solution, the bubbles in the overhead product are collapsed, and the fractionation process of claim 1 is repeated using a solution which is prepared from the overhead product.

13. The process of claim 12 wherein the process of claim 12 is repeated at least once.

14. The process of claim 10 wherein after said moving step, the pool is recovered as a bottoms product containing a mixture of optical isomers which is enriched in one of the enantiomers or diastereomers as compared to the starting solution, and the fractionation process of claim 1 is repeated using a solution which is prepared from the bottoms product.

15. The process of claim 14 wherein the process of claim 14 is repeated at least once.

16. A process for enriching the concentration of an enantiomer in a mixture of optically active isomers, the process comprising:

preparing a solution containing the mixture of the optically active isomers and a chiral collector in which the chiral collector and the enantiomer are associated with each other and in which there are simultaneously at least 3 points of interaction between the chiral collector and the enantiomer with one of the points of interaction involving a hydrophobic region of the chiral collector, bubbling a gas through a pool of the solution to form a foam, the surfaces of the bubbles of the foam having an inclusion complex of the chiral collector and the enantiomer preferentially adsorbed thereto, so that the concentration ratio of the optically active isomers at said bubble surfaces differs from that in the bulk of the pool, and moving said foam vertically through the gas-space above the upper surface of the pool.

17. A process for enriching the concentration of an enantiomer or a diastereomer in a mixture of optically active isomers, the process comprising:

preparing a solution containing the mixture of the optically active isomers and a chiral collector in which the chiral collector and the enantiomer or diastereomer are associated with each other, bubbling a gas through a pool of the solution to form bubbles, the surfaces of the bubbles having the chiral collector and the enantiomer or diastereomer preferentially adsorbed thereto so that the concentration ratio of the optically active isomers at said bubble surface differs from that in the bulk of the pool, moving said bubbles vertically through the gas-space above the upper surface of the pool, and thereafter recovering the optical isomer of the mixture from the pool which is present in the greatest quantity.

* * * * *